(12) United States Patent
Wada et al.

(10) Patent No.: US 10,076,278 B2
(45) Date of Patent: Sep. 18, 2018

(54) HEADBAND, HEADGEAR, AND ELECTROENCEPHALOGRAPHIC APPARATUS

(71) Applicant: Sony Corporation, Tokyo (JP)

(72) Inventors: Seiji Wada, Kanagawa (JP); Mitsuhiro Nakamura, Kanagawa (JP); Natsuki Kimura, Tokyo (JP); Haruhiko Soma, Tokyo (JP); Yusaku Nakashima, Tokyo (JP); Takuro Yamamoto, Kanagawa (JP); Takashi Tomita, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 587 days.

(21) Appl. No.: 14/349,996

(22) PCT Filed: Sep. 18, 2012

(86) PCT No.: PCT/JP2012/005937
§ 371 (c)(1),
(2) Date: Apr. 4, 2014

(87) PCT Pub. No.: WO2013/054472
PCT Pub. Date: Apr. 18, 2013

(65) Prior Publication Data
US 2014/0249385 A1    Sep. 4, 2014

(30) Foreign Application Priority Data

Oct. 14, 2011 (JP) .................... 2011-227204

(51) Int. Cl.
*A61B 5/04* (2006.01)
*A61B 5/00* (2006.01)
*A61B 5/0478* (2006.01)
*A61B 5/08* (2006.01)
*A61B 5/145* (2006.01)

(52) U.S. Cl.
CPC .......... *A61B 5/6803* (2013.01); *A61B 5/0478* (2013.01); *A61B 5/08* (2013.01); *A61B 5/14542* (2013.01); *A61B 2560/045* (2013.01); *A61B 2562/12* (2013.01)

(58) Field of Classification Search
CPC ..... A61B 5/6803; A61B 5/14542; A61B 5/08; A61B 5/0478; A61B 2562/12; A61B 2560/045
See application file for complete search history.

(56) References Cited

U.S. PATENT DOCUMENTS 1,905,370 A    4/1933   Dorsey et al.
5,406,956 A    4/1995   Farwell
(Continued)

FOREIGN PATENT DOCUMENTS

JP    2009-530064        8/2009
JP    WO 2011/02093  *  1/2011  ........... A61B 5/0492
(Continued)

*Primary Examiner* — Tiffany Weston
(74) *Attorney, Agent, or Firm* — Chip Law Group

(57) ABSTRACT

To provide a headband capable of correctly placing an electrode on a head of a user, a headband apparatus includes a plurality of headband portions integrally connected and configured to be positioned about a head of a user, wherein at least two headband portions are each configured to be positioned behind an ear.

11 Claims, 11 Drawing Sheets

(56) References Cited

U.S. PATENT DOCUMENTS

| | | | |
|---|---|---|---|
| 5,479,934 A | 1/1996 | Imran | |
| 6,077,237 A * | 6/2000 | Campbell | G06F 3/011 |
| | | | 600/587 |
| 2009/0024017 A1 * | 1/2009 | Ruffini | A61B 5/0408 |
| | | | 600/395 |
| 2010/0274152 A1 | 10/2010 | McPeck | |
| 2011/0098593 A1 * | 4/2011 | Low | A61B 5/0478 |
| | | | 600/544 |
| 2012/0190959 A1 * | 7/2012 | Hayakawa | A61B 5/0478 |
| | | | 600/383 |

FOREIGN PATENT DOCUMENTS

| | | |
|---|---|---|
| JP | 2011-104338 | 6/2011 |
| WO | 2011/002093 | 1/2011 |

\* cited by examiner

HEADBAND, HEADGEAR, AND ELECTROENCEPHALOGRAPHIC APPARATUS

CROSS REFERENCES TO RELATED APPLICATIONS

The present application is a national stage of International Application No. PCT/JP2012/005937 filed on Sep. 18, 2012 and claims priority to Japanese Patent Application No. 2011-227204 filed on Oct. 14, 2011, the disclosure of which is incorporated herein by reference.

BACKGROUND

The present disclosure relates to a headband for placing an electrode on the head of a user, a headgear including the headband, and an electroencephalographic apparatus including the headgear.

Brain waves are electrical signals generated due to the brain activity of the user and can be measured by electrodes connected to predetermined positions of the head of the user. In order to place the electroencephalogram electrodes in the predetermined positions of the head, a headgear on which a plurality of electroencephalogram electrodes are set in advance is often used.

For example, Japanese Patent Application Laid-open No. 2011-104338 discloses a headgear including an I-shaped frame extending from the frontal region of the user through the parietal region to the occipital region. This headgear has such a configuration that the frame and electrodes provided to arms of the frame are placed in predetermined positions of the head of the user.

Further, Japanese Unexamined Patent Application Publication No. 2009-530064 discloses an electrode headset including rigid bands covering a large part of the head of the user and electrode mounts in which electrodes can be mounted. This electrode headset has such a configuration that the electrodes mounted in the electrode mounts are exchangeable.

CITATION LIST

Patent Literature

[PTL 1]
Japanese Patent Application Laid-open No. 2011-104338
[PTL 2]
Japanese Unexamined Patent Application Publication No. 2009-530064

SUMMARY

There is a fear that the headgear or the headset as described above may be misaligned from its attachment position in electroencephalogram measurement during sleep of the user due to contact of the head of the user with a pillow, which would not cause problems in electroencephalogram measurement during waking hours of the user. Moreover, when a different user wears the headgear or the headset as described above, there is a fear that the headgear or the headset may not fit him and may not be reliably fixed.

In the above-mentioned circumstances, there is a need for providing a headband capable of correctly placing an electrode on the head of a user, a headgear including the headband, and an electroencephalographic apparatus including the headgear.

According to an embodiment of the present disclosure, there is provided a headgear apparatus including a plurality of headband portions. The plurality of headband portions are integrally connected and configured to be positioned about a head of a user, wherein at least two headband portions are each configured to be positioned behind an ear.

With this configuration, when the headband apparatus is attached to the head of the user, a first headband portion is placed to extend from the forehead of the user to an upper portion of the occipital region and a second headband portion and the third headband portion branch off in opposite directions from the upper portion of the occipital region and arrive at the left and right mastoid regions (conical protrusions located at lower rear portions of temporal bones). That is, the headband apparatus is placed not to cover from the connection point of the respective headband portions in the upper portion of the occipital region to the lower portion of the occipital region. With this, when the user wearing the headgear sleeps while lying on his back, the headband does not abut against a pillow. Thus, it becomes possible to prevent misalignment of the headband, that is, detachment of the electrode due to contact with the pillow.

In some embodiments, the at least two headband portions are spaced apart so as to be adapted to define an open area on a back region of the head, the open area including a parietal and an occipital region of the head. Further, the at least two headband portions may be configured to be positioned about a mastoid region of the head.

In some additional embodiments, the headband apparatus further includes at least one headband portion configured to be positioned about a forehead region of the head. In these embodiments the at least one headband portion includes a first end configured to contact the forehead region and a second end configured to contact an upper portion of the occipital region. Additionally, the at least two headband portions each include a third end connected to the second end of the first headband part and a fourth end that is configured to contact the mastoid region. In these embodiments the headband apparatus may further include a plurality of abutting parts connected respectively to the fourth end of the at least two headband portions, the abutting parts including an elastic material configured to position the at least two headband portions to the mastoid region. Moreover, the headband apparatus may further include an abutting part connected to the first end of the at least one headband portion, the abutting part including an elastic material configured to position the at least one headband portion to the forehead region.

With this configuration, the headband apparatus is supported to hold the head of the user at the three points of the first abutting part, the second abutting part, and the third abutting part with an elastic force. Therefore, even if the headband apparatus strains due to roll-over of the user or the like so that an electrode is detached, it becomes possible that the elastic force of the headband restores its shape so that the electrical contact of the electrode is restored.

According to another embodiment, a headgear apparatus includes a plurality of headband portions integrally connected and configured to be positioned about a head of a user, wherein at least two headband portions are each configured to be positioned behind an ear. The headgear apparatus also includes a plurality of electrodes included within some of the headband portions that are configured to measure an electrical activity of the head.

The electrodes may include a right reference electrode that is placed on the second abutting part to detect a reference potential, and a left reference electrode that is placed on the third abutting part to detect a reference potential.

Although the reference electrode in electroencephalogram measurement should be placed in a site of the head of the user, on which the brain waves are less influential, the left and right mastoid regions are suitable for placing the reference electrode. Therefore, the left and right reference electrodes are placed on the second abutting part and the third abutting part, and hence it is unnecessary to additionally place the reference electrodes, and only by wearing the headgear, the placement of the reference electrodes becomes possible.

According to another embodiment of the present disclosure, there is provided an electroencephalographic apparatus including a plurality of headband portions integrally connected and configured to be positioned about a head of a user, wherein at least two headband portions are each configured to be positioned behind an ear. The headgear apparatus also includes a plurality of electrodes included within some of the headband portions are configured to measure an electrical activity of the head. The headgear apparatus further includes a main body connection part included within at least one of the headband portions and electrically connected to the plurality of electrodes, the main body connection part configured to accommodate a detachable main body. The main body is detachably connected to the headgear and houses an electronic circuit that processes an output signal of the electrode.

With this configuration, it becomes possible to attach/detach the main body to/from the headgear apparatus and also use a main body having a different configuration.

The main-body connection part may include a screw hole, a tubular skirt that is provided around the screw hole and is formed of a flexible material, and a tubular guide that is provided around the skirt and is formed of a non-flexible material.

With this configuration, the main body to be connected to the main-body connection part is supported on the headgear apparatus with flexibility, and hence it becomes possible to connect the main body without interfering with the elastic deformation of the headband. The flexible skirt protects a wiring between the main body and the headgear and the guide prevents excessive tilting of the main body with respect to the headgear.

According to an embodiment of the present disclosure, there is provided a headband including a first headband part, a second headband part, and a third headband part. The first headband part extends from a forehead of a user to an upper portion of an occipital region of the user. The second headband part is connected to the first headband part and extends from the upper portion of the occipital region of the user, orthogonally to the first headband part, to a right mastoid region of the user. The third headband part is connected to the first headband part and extends from the upper portion of the occipital region of the user, orthogonally to the first headband part, to a left mastoid region of the user.

As described above, according to the present disclosure, it becomes possible to provide a headband capable of correctly placing an electrode on the head of a user, a headgear including the headband, and an electroencephalographic apparatus including the headgear.

Additional features and advantages are described herein, and will be apparent from the following Detailed Description and the figures.

DETAILED DESCRIPTION

An electroencephalographic apparatus according to an embodiment of the present disclosure will be described.
[Configuration of Electroencephalographic Apparatus]

Figure 1:
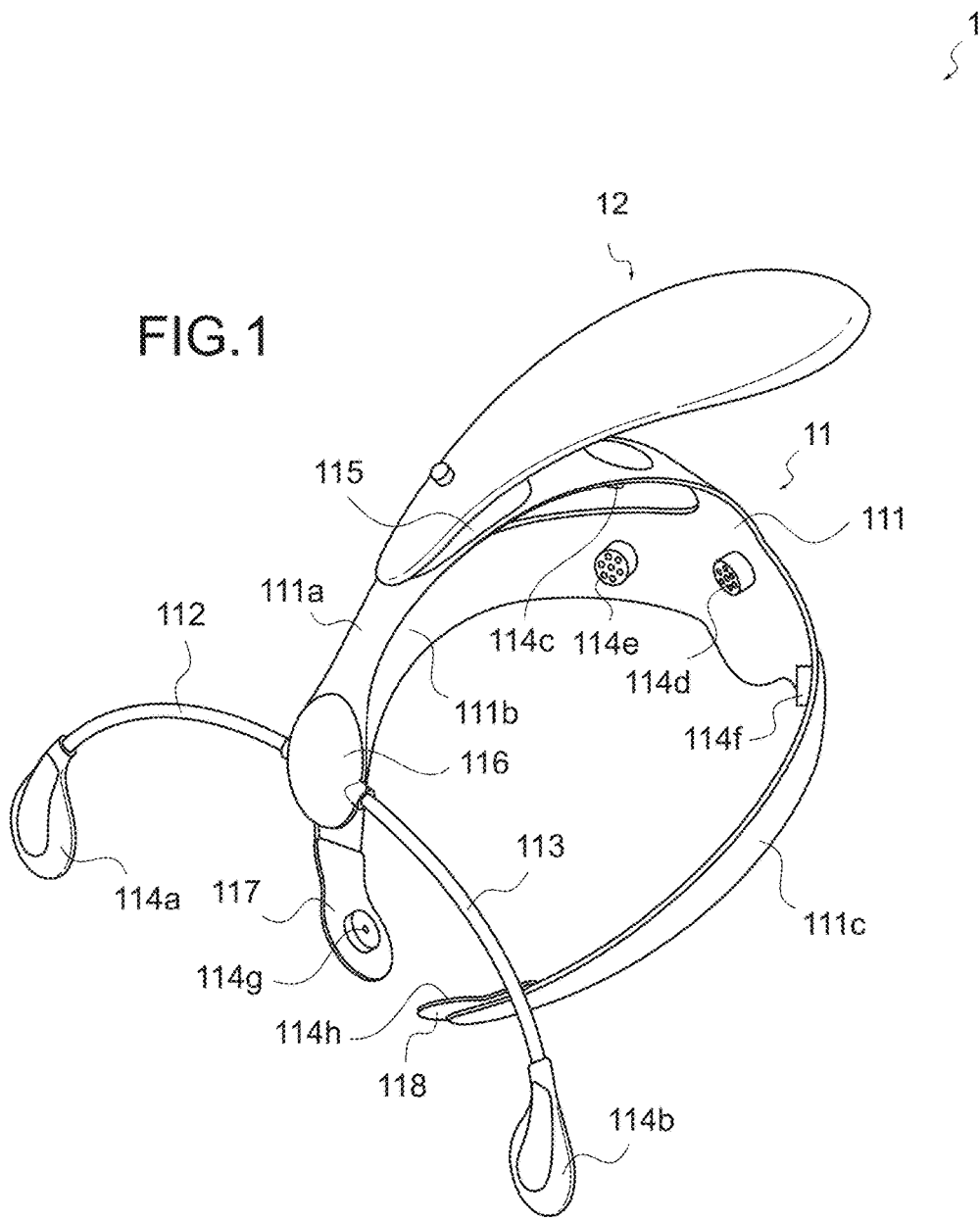
FIG. 1 is a perspective view showing an outer appearance of an electroencephalographic apparatus according to an embodiment of the present disclosure.
Figure 2:
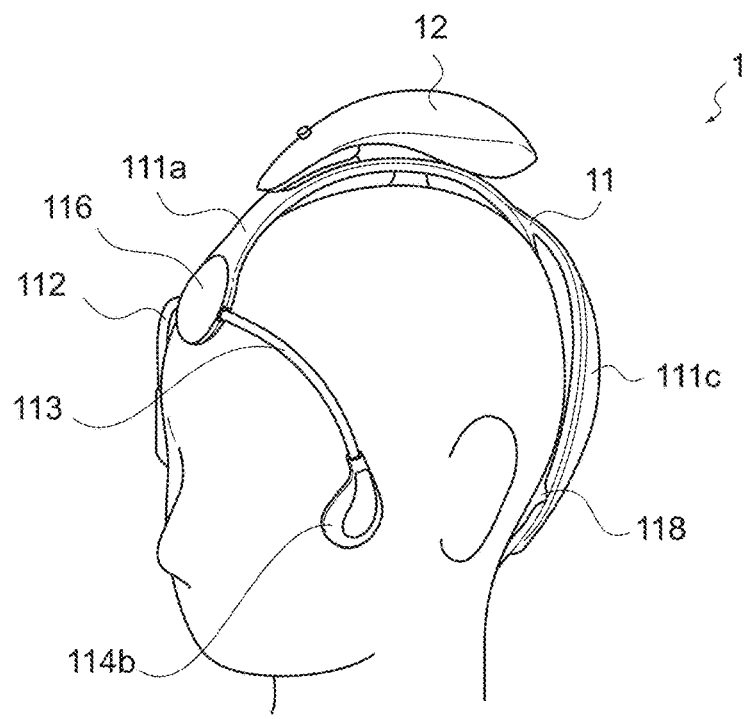
FIG. 2 is a perspective view showing a state of the electroencephalographic apparatus worn by a user.
Figure 3:
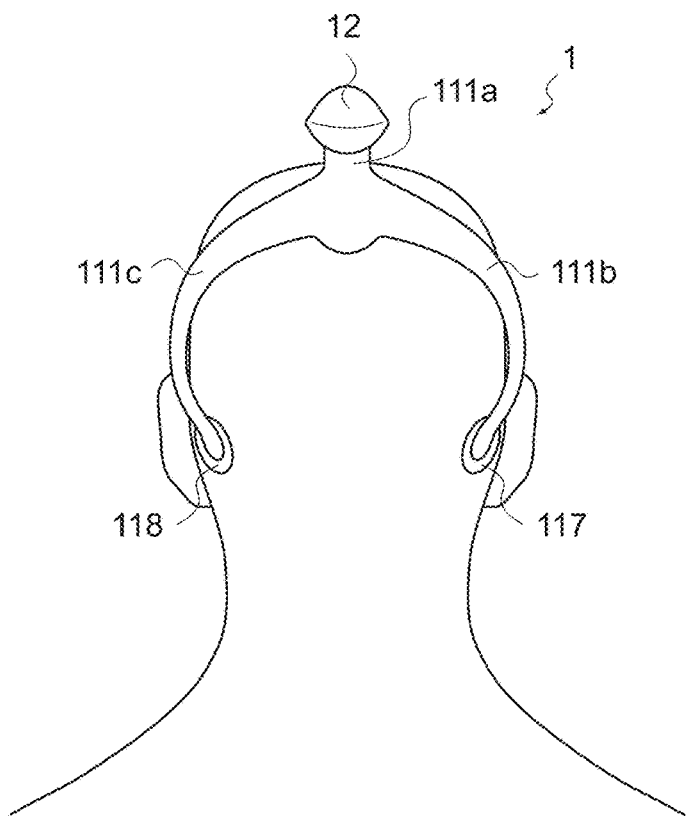
FIG. 3 is a perspective view showing a state of the electroencephalographic apparatus worn by the user.

FIG. 1 is a perspective view showing an outer appearance of an electroencephalographic apparatus 1 according to this embodiment. FIGS. 2 and 3 are outer views each showing the electroencephalographic apparatus 1 worn by a user. FIG. 2 is a view of the electroencephalographic apparatus 1 as viewed from a left-hand side of the user and FIG. 3 is a view of the electroencephalographic apparatus 1 as viewed from the back side of the user. As shown in these figures, the electroencephalographic apparatus 1 includes a headgear 11 and a main body 12. The main body 12 is detachably connected to the headgear 11. Portions of the headgear 11 are spaced apart so as to be adapted to define an open area on a back region of a head of the user. The open area can include, for example, a parietal and an occipital region of the head. In other examples, the open area can include additional regions or fewer regions of the head.

Figure 4:
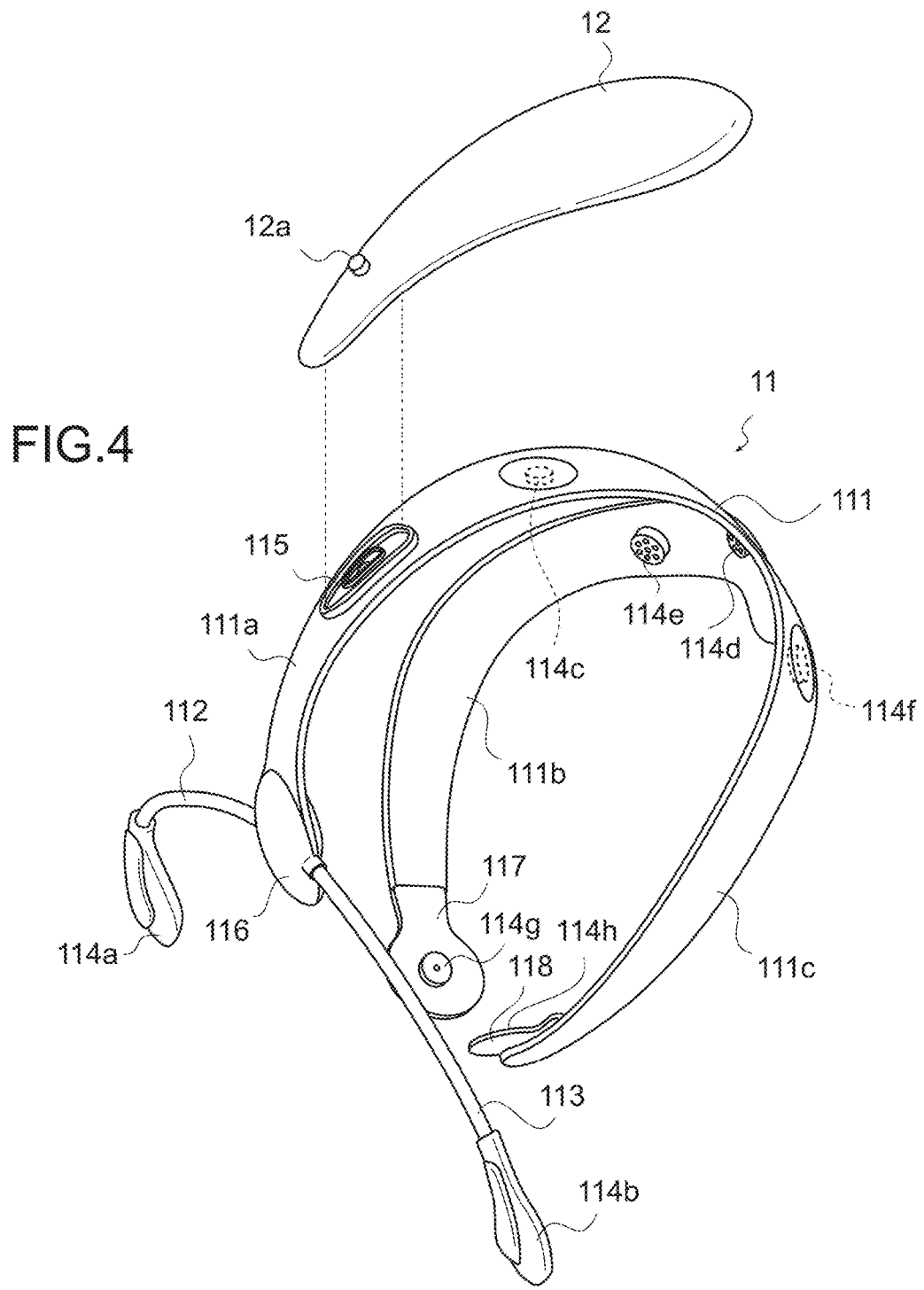
FIG. 4 is an exploded perspective view of the electroencephalographic apparatus.

FIG. 4 is an exploded perspective view of the electroencephalographic apparatus 1. As shown in the figure, the headgear 11 includes a headband 111, a right arm 112, a left arm 113, various electrodes 114a to 114h, a main-body connection part 115, a first abutting part 116, a second abutting part 117, and a third abutting part 118.

The right arm 112 and the left arm 113 are connected to the headband 111. The various electrodes 114a to 114h are provided to any of the headband 111, the right arm 112, and the left arm 113. The main-body connection part 115 is provided to the headband 111. The first abutting part 116, the second abutting part 117, and the third abutting part 118 are provided to each end portion of the headband 111.

The headband 111 is formed of an elastic material, for example, a synthetic resin and includes a first headband part 111a, a second headband part 111b, and a third headband part 111c.

The first headband part 111a is, as shown in FIGS. 2 and 3, a plate-like member extending from the forehead of the user to the upper portion of the occipital region and is formed to have a curved shape conforming to the shape of the head. At the end portion of the first headband part 111a, the first abutting part 116 that abuts against the forehead of the user is provided. The first abutting part 116 may be formed of an elastic material such as a sponge or rubber.

The second headband part 111b is, as shown in FIGS. 2 and 3, a plate-like member extending from the upper portion of the occipital region of the user, orthogonally to the first headband part 111a, to the right mastoid region (conical protrusion located at lower rear portion of temporal bone) of the user. The second headband part 111b is formed to have a curved shape conforming to the shape of the head. At the end portion of the second headband part 111b, the second abutting part 117 that abuts against the right mastoid region of the user is provided. The second abutting part 117 may be formed of an elastic material such as a sponge or rubber.

The third headband part 111c is, as shown in FIGS. 2 and 3, a plate-like member extending from the upper portion of the occipital region of the user, orthogonally to the first headband part 111a, to the left mastoid region of the user. The third headband part 111c is formed to have a curved shape conforming to the shape of the head. At the end portion of the third headband part 111c, the third abutting part 118 that abuts against the left mastoid region of the user. The third abutting part 118 may be formed of an elastic material such as a sponge or rubber.

The headband 111 includes, as described above, the first headband part 111a, the second headband part 111b, and the third headband part 111c and is attached to the head of the user with an elastic force. At this time, the first abutting part 116 is pressed against the forehead of the user, the second abutting part 117 is pressed against the right mastoid region of the user, and the third abutting part 118 is pressed against the left mastoid region of the user, such that the headgear 11 is supported at these points.

The first headband part 111a, the second headband part 111b, and the third headband part 111c are connected to one another in a T-shape and have a shape branching off in left- and right-hand directions in the upper portion of the occipital region of the user. With this, when the user sleeps while lying on his back, the headband 111 is not held in contact with a pillow, and hence misalignment of the headgear 11 does not occur. Therefore, it becomes possible to stably measure electrooculogram and the apparatus does not disturb user's sleep.

The right arm 112 is an arm for supporting a right EEG electrode 114a (to be described later) that is placed on the right temple of the user. The right arm 112 may have a shape extending from a right side surface of the first abutting part 116 of the first headband part 111a toward the right temple. It should be noted that in the case where the right EEG electrode 114a is not provided, the right arm 112 may not be essential.

The left arm 113 is an arm for supporting a left EEG electrode 114b (to be described later) that is placed on the left temple of the user. The left arm 113 may have a shape extending from a left side surface of the first abutting part 116 of the first headband part 111a toward the left temple. It should be noted that in the case where the left EEG electrode 114b is not provided, the left arm 113 may not be essential.

The electrodes 114a to 114h are various electrodes provided to the headgear 11. As the electrodes 114a to 114h, in addition to the right EEG electrode 114a and the left EEG electrode 114b, a Cz measurement electrode 114c, a Pz measurement electrode 114d, a P4 measurement electrode 114e, a P3 measurement electrode 114f, a right reference electrode 114g, and a left reference electrode 114h may be provided. This placement (name) complies with the International 10-20 system. However, in the electroencephalographic apparatus 1 according to this embodiment, this electrode placement may not be essential and different electrode placement may be possible depending on needs.

The right EEG electrode 114a and the left EEG electrode 114b are electrodes that abut against both the temples of the user to measure eye movement (electrooculogram (EOG)). The right EEG electrode 114a and the left EEG electrode 114b only need to be capable of establishing electrical contact with the temples of the user and may be each formed of, for example, an elastic body impregnated with an electrolytic solution.

The Cz measurement electrode 114c is an electrode that is provided in a position of the first headband part 111a that corresponds to the parietal region, and abuts against the parietal region of the user. The Pz measurement electrode 114d is an electrode that is provided in a position of the first headband part 111a that corresponds to the upper portion of the occipital region, and abuts against the upper portion of the occipital region of the user.

The P4 measurement electrode 114e is an electrode that is provided in a position of the second headband part 111b that corresponds to the upper right head region, and abuts against the upper right head region of the user. The P3 measurement electrode 114f is an electrode that is provided in a position of the third headband part 111c that corresponds to the upper left head region, and abuts against the upper left head region of the user.

The Cz measurement electrode 114c, the Pz measurement electrode 114d, the P4 measurement electrode 114e, and the P3 measurement electrode 114f only need to be capable of establishing electrical contact with the scalp of the user and may be each formed of, for example, an elastic body impregnated with an electrolytic solution. The Cz measurement electrode 114c, the Pz measurement electrode 114d, the P4 measurement electrode 114e, and the P3 measurement electrode 114f detect potentials (brain waves) of their in-contact positions.

The right reference electrode 114g is an electrode that is provided to the second abutting part 117 and abuts against the right mastoid region of the user. The left reference electrode 114h is an electrode that is provided to the third abutting part 118 and abuts against the left mastoid region of the user. The right reference electrode 114g and the left reference electrode 114h only need to be capable of establishing electrical contact with the left and right mastoid regions of the user and may be each formed of, for example, an elastic body impregnated with an electrolytic solution. The right reference electrode 114g and the left reference electrode 114h acquire each reference potential of the electrodes 114a to 114f.

It should be noted that the right reference electrode 114g is placed on the second abutting part 117 and the left reference electrode 114h is placed on the third abutting part 118, and hence these reference electrodes are placed only by attaching the headgear 11 to the head of the user. Therefore, it is unnecessary to additionally placing these reference electrodes after attachment of the headgear 11, which is highly convenience.

Each of the electrodes 114a to 114h may be connected to the main-body connection part 115 via a wiring (not shown), so that when the main body 12 is mounted on the main-body connection part 115, those electrodes can be electrically connected to the main body 12.

Figure 5:
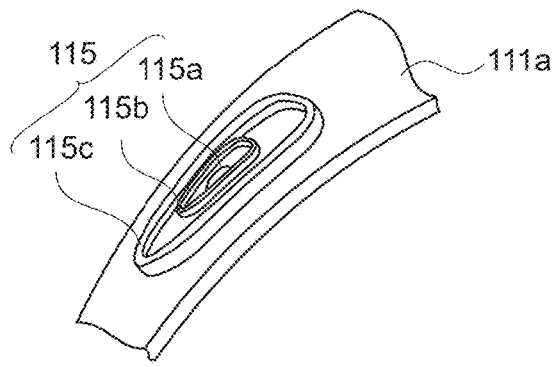
FIG. 5 is a perspective view showing a main-body connection part of the electroencephalographic apparatus.

The main-body connection part 115 is provided to the first headband part 111a so that the main body 12 can be detachably connected thereto. FIG. 5 is a perspective view showing the main-body connection part 115. As shown in the figure, the main-body connection part 115 supports the main body 12 at a single point, and hence the main-body connection part 115 can support the main body 12 without deteriorating the flexibility of the first headband part 111a or the like.

Specifically, the main-body connection part 115 includes a screw hole 115a, a skirt 115b, and a guide 115c. The skirt 115b is provided around the screw hole 115a and the guide 115c is, in turn, provided around the skirt 115b. The skirt 115b is a tubular member made of a flexible material such as an elastomer. The guide 115c is a tubular member made of a non-flexible material such as a synthetic resin.

The main body 12 is screwed into the screw hole 115a with a screw 12a to be connected to the main-body connection part 115. With this, the main body 12 is supported with certain flexibility and the guide 115c prevents excessive tilting of the main body 12 with respect to the main-body connection part 115. In addition, the skirt 115b protects the wiring between the main body 12 and the main-body connection part 115 and does not interfere with the flexibility of the main body 12 with respect to the main-body connection part 115.

By configuring the main-body connection part 115 as described above, when the headband 111 is deformed conforming to the shape of the head of the user, the main body 12 does not interfere with the deformation of the headband 111. If the main-body connection part 115 is connected to the headband 111 at a plurality of points, the elastic deformation of the headband 111 is interfered with. That is, the main-body connection part 115 according to this embodiment has a structure of supporting the main body at the single point, and hence it becomes possible to cause the headband 111 to fit the head of the user.

Figure 6:
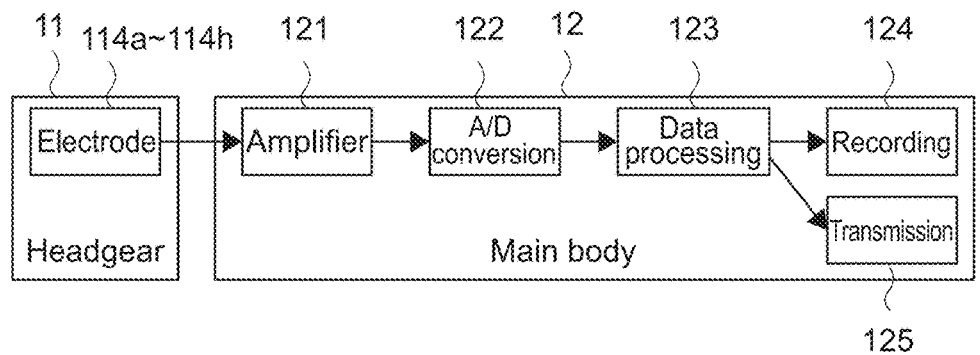
FIG. 6 is a schematic view showing a functional configuration of the electroencephalographic apparatus.

The main body 12 is connected to the headgear 11 for use as described above. FIG. 6 is a schematic view showing a functional configuration of the electroencephalographic apparatus 1. As shown in the figure, the main body 12 is equipped with an amplifier 121, an A/D (Analog/Digital) converter 122, a data processing circuit 123, a recorder 124, and a transmitter 125.

An electrical signal acquired by each of the electrodes 114a to 114h of the headgear 11 passes through the main-body connection part 115 and arrives at the main body 12. The electrical signal is amplified by the amplifier 121 and is converted by the A/D converter 122 into a digital signal. Then, the digital signal is subjected to data processing such as montage (difference output between measurement electrode and reference electrode) by the data processing circuit 123. By such processing, electroencephalogram data is acquired.

The electroencephalogram data is stored by the recorder 124 on a built-in memory or a memory card or transmitted by the transmitter 125 to an external device. It should be noted that the functional configuration of the main body 12 as described above is an example and a different configuration may be possible.

As described above, the main body 12 is configured to be attachable/detachable to/from the headgear 11, which has the following advantages. Firstly, it becomes possible to individually upgrade the main body 12 or the headgear 11.

Figure 7:
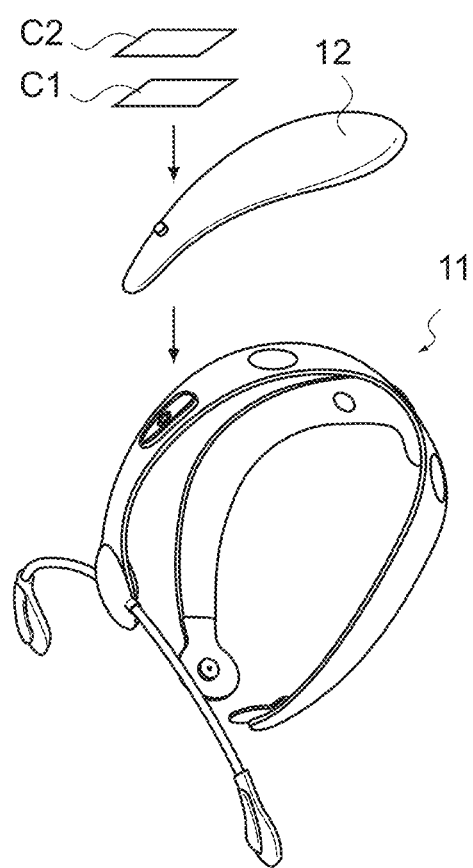
FIG. 7 is a schematic view showing a state of the electroencephalographic apparatus including an upgraded headgear.
Figure 8:
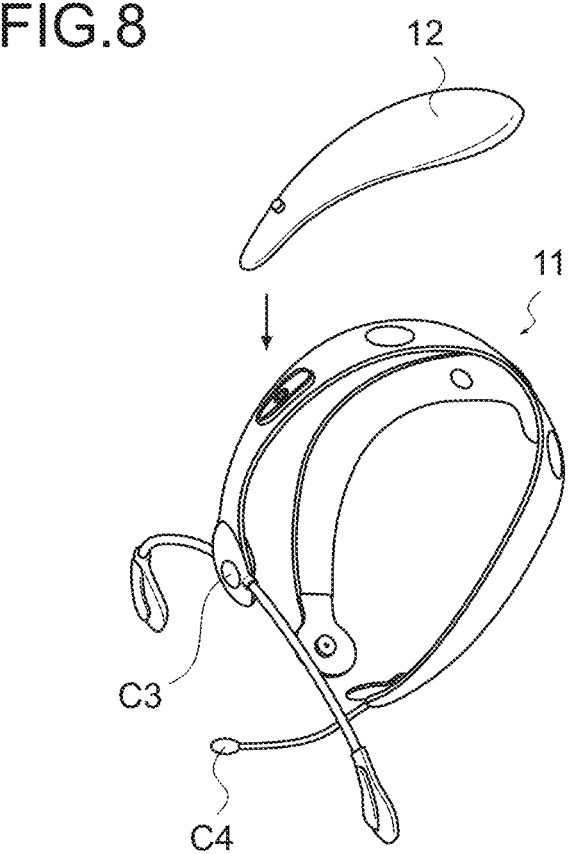
FIG. 8 is a schematic view showing a state of the electroencephalographic apparatus including a main body.

FIG. 7 is a schematic view showing an example in which the main body 12 is upgraded. FIG. 8 is a schematic view showing an example in which the headgear 11 is upgraded. As shown in these figures, by providing circuits C1 and C2 capable of measuring additional measurement items (e.g., arterial oxygen saturation or naso-oral breathing measurement) to the main body 12 or by providing sensors C3 and C4 capable of measuring the additional measurement items to the headgear 11, it becomes possible to measure these additional measurement items.

Secondly, it is possible to use the headgear 11 having a size suitable for each user. For example, in the case where a plurality of users use the electroencephalographic apparatus 1, once the headgears 11 each having a size suitable for each user are prepared, the single main body 12 can be shared by the users. It contributes to reduce the costs in comparison with a case where the electroencephalographic apparatuses 1 are prepared for the respective users.

Figure 9:
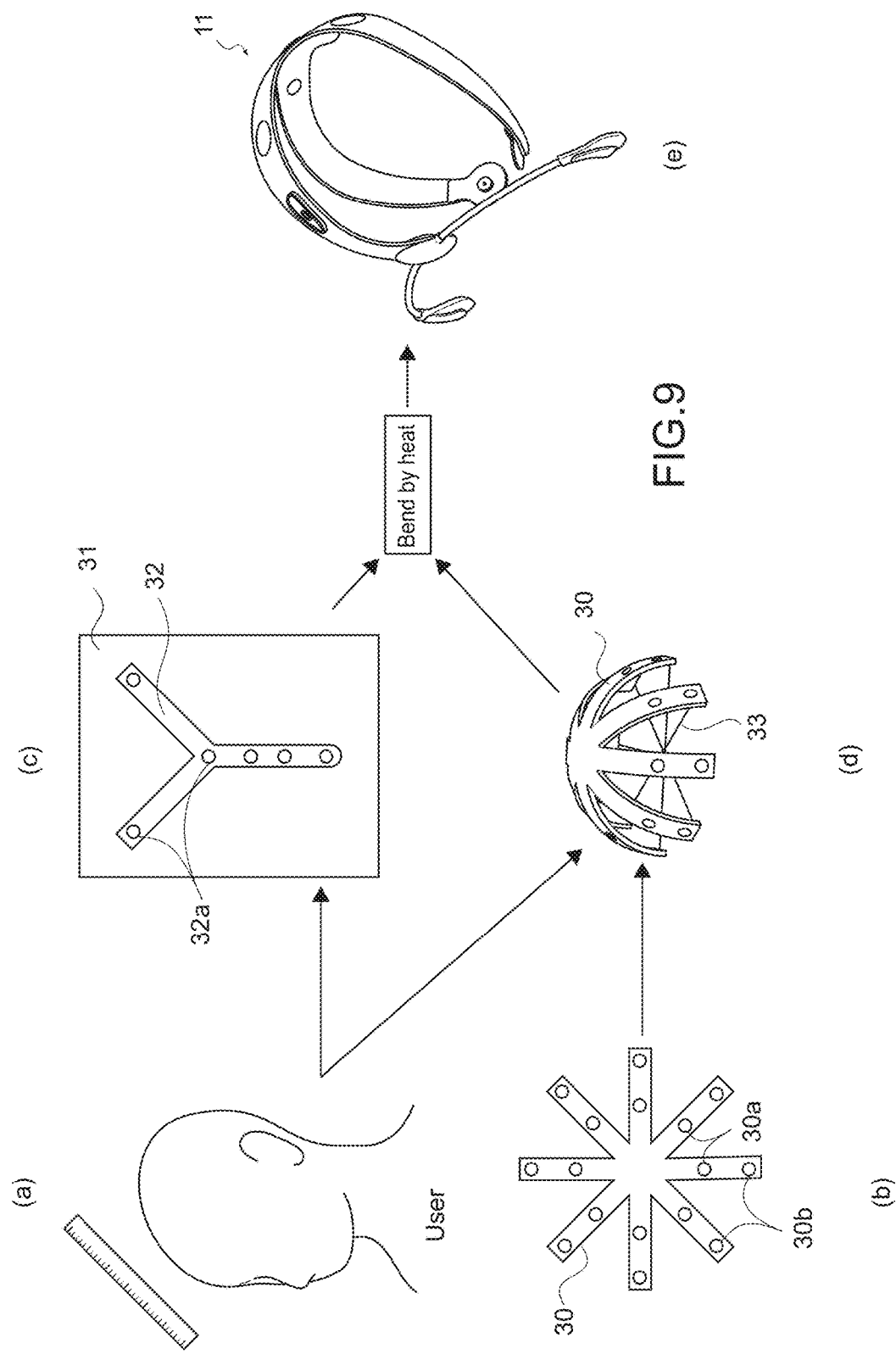
FIG. 9 is a schematic view showing how to produce the headgear of the electroencephalographic apparatus.

For the headgear 11 having the size suitable for each user, a headgear may be selected among headgears having a plurality of sizes, for example, S, M, L, and the like. Alternatively, in the following manner, it is also possible to produce the headgear for each user (made-to-order production system). FIG. 9 is a schematic view showing how to produce the headgear 11 in the made-to-order production system.

First, as shown in (a) of FIG. 9, the shape of the head of the user is measured. Further, as shown in (b) of FIG. 9, a head pattern 30 made of a heat-resistant material is prepared. The head pattern 30 is formed to have a radially extending eight-band-like shape. Holes 30a for curve of the head and holes 30b for diameter of the head are formed in the bands.

In addition, as shown in (c) of FIG. 9, a plastic plate 31 is cut into a cut plate 32 having a shape of the headband 111. In the cut plate 32, electrode/main body mounting holes 32a are formed. Further, as shown in (d) of FIG. 9, a pattern is shaped by bending the head pattern 30 to have a shape slightly smaller than the shape of the head and pulling it by wires 33.

The headgear 11 is produced by bending the cut plate 32 by heat with the head pattern 30 being used as a pattern and by mounting the electrodes 114a to 114h, the main-body connection part 115, and the like, as shown in (e) of FIG. 9. The thus produced headgear 11 conforms to the shape of the head of the user.

Figure 10:
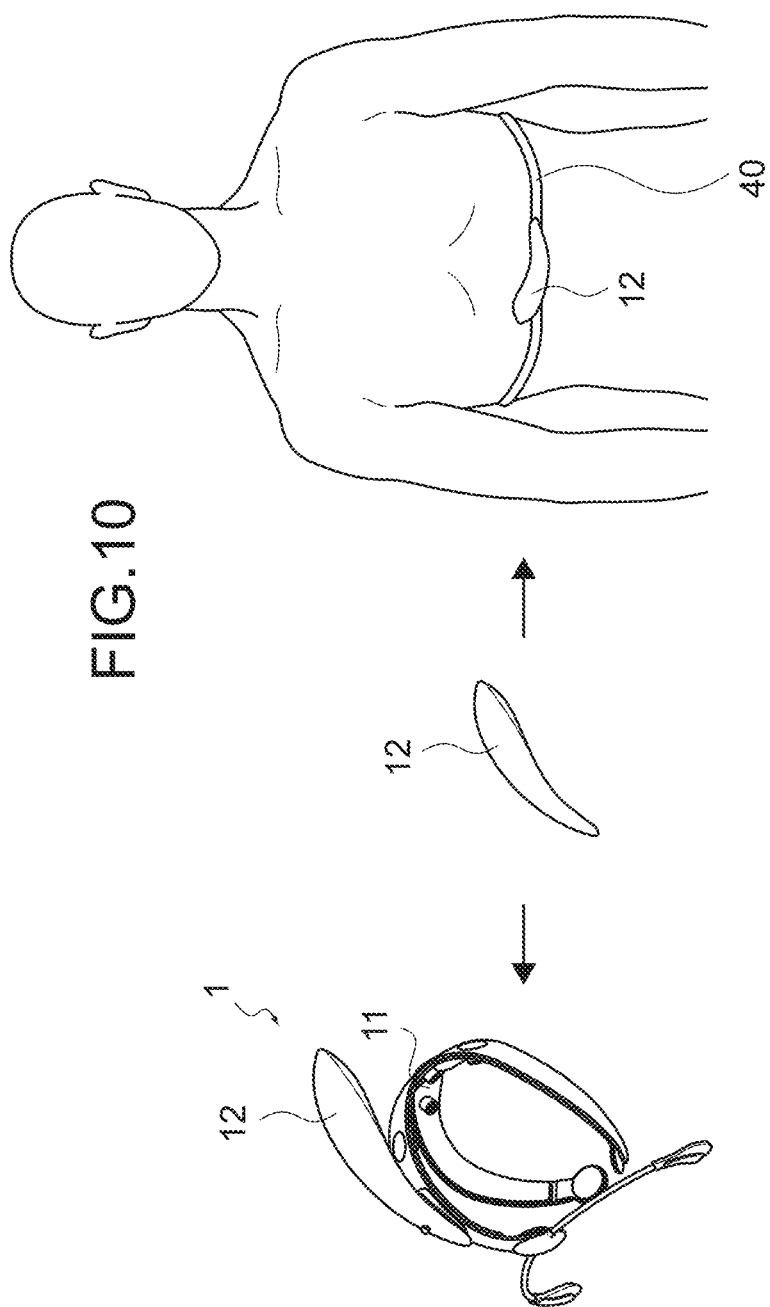
FIG. 10 is a schematic view showing an application change of the main body of the electroencephalographic apparatus.

Thirdly, it becomes possible to use the main body 12 for applications other than the electroencephalograph. FIG. 10 is a schematic view showing an application change of the main body 12. FIG. 10 shows the main body 12 connected to an accessory 40 wound around the body of the user. As shown in the figure, by changing the accessory on which the electrodes are mounted, for example, it becomes possible to use the main body 12 as a main body of an electrocardiograph or an electromyograph.

Figure 11:
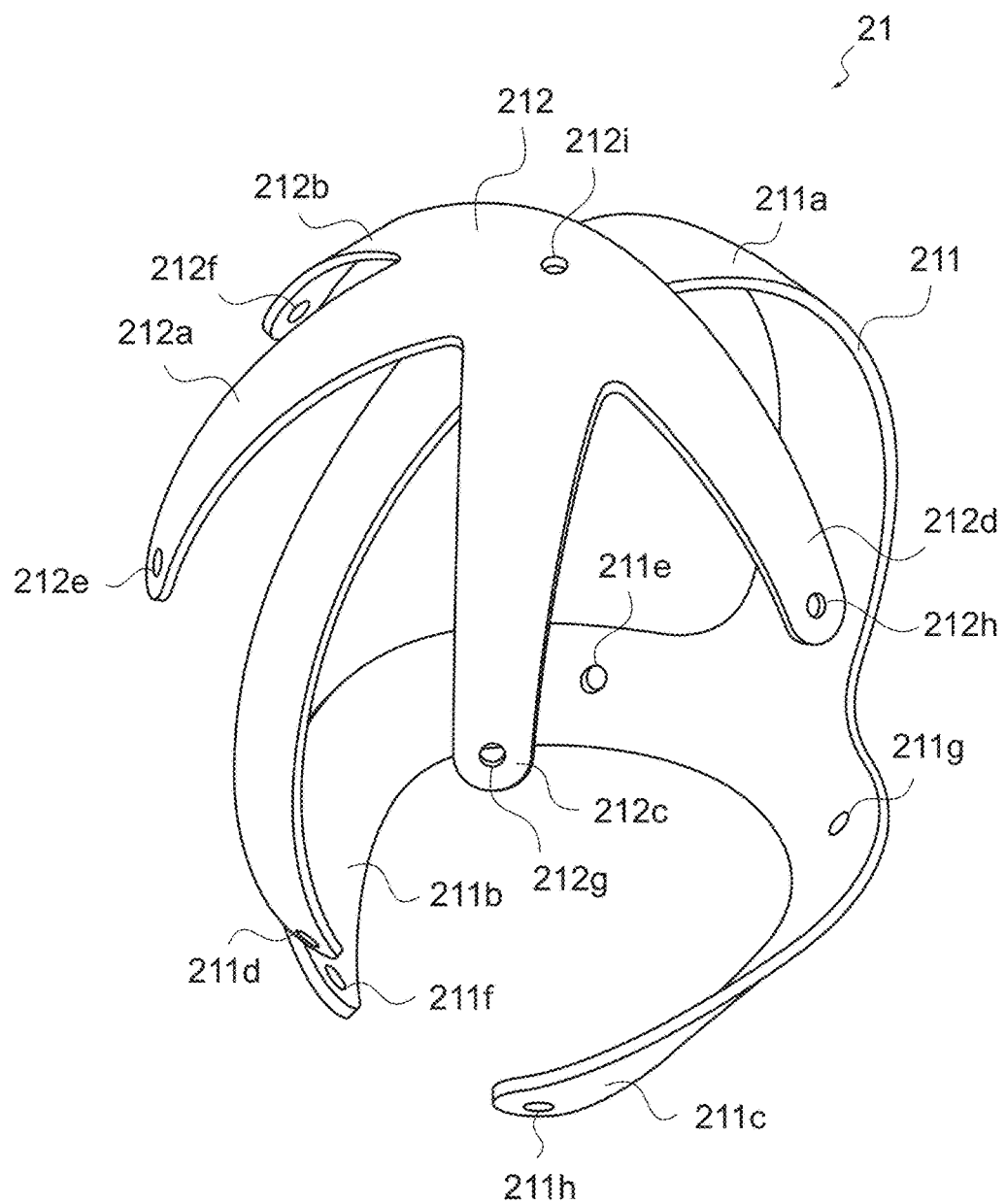
FIG. 11 is a schematic view showing a six-electrode headgear capable of connecting the main body of the electroencephalographic apparatus.

Further, it is also possible to connect the main body 12 to the headgear having a different shape. FIG. 11 is a perspective view showing a six-electrode headgear 21 capable of connecting the main body 12. As shown in the figure, the six-electrode headgear 21 includes two members of a headband 211 and an electrode mount 212. The electrode mount 212 is connected to the headband 211 in a position corresponding to the parietal region of the user.

The headband 211 is formed of an elastic material, for example, a synthetic resin and includes a first headband part 211a, a second headband part 211b, and a third headband part 211c.

The first headband part 211a is a plate-member extending from the forehead of the user to the lower portion of the occipital region and is formed to have a curved shape conforming to the shape of the head. The first headband part 211a is provided with a hole 211d for fixing a reference electrode.

The second headband part 211b is a plate-like member extending from the lower portion of the occipital region of the user, orthogonally to the first headband part 211a, to a lower portion of the right earlobe of the user. The second headband part 211b is formed to have a curved shape conforming to the shape of the head. The second headband part 211b is provided with a hole 211e for fixing an O2 measurement electrode and a hole 211f for fixing a right reference electrode.

The third headband part 211c is a plate-like member extending from the lower portion of the occipital region of the user, orthogonally to the first headband part 211a, to the lower portion of the left earlobe of the user. The third headband part 211c is formed to have a curved shape conforming to the shape of the head. The third headband part 211c is provided with a hole 211g for fixing an O1 measurement electrode and a hole 211h for fixing a left reference electrode.

The electrode mount 212 is formed of an elastic material, for example, a synthetic resin and includes a first mount part 212a, a second mount part 212b, a third mount part 212c, and a fourth mount part 212d.

The first mount part 212a is a plate-like member extending from the parietal region of the user to an F4 measurement electrode and is formed to have a curved shape conforming to the shape of the head. The first mount part 212a is provided with a hole 212e for fixing an F4 measurement electrode.

The second mount part 212b is a plate-like member extending from the parietal region of the user to a C4 measurement electrode and is formed to have a curved shape conforming to the shape of the head. The second mount part 212b is provided with a hole 212f for fixing a C4 measurement electrode.

The third mount part 212c is a plate-like member extending from the parietal region of the user to an F3 measurement electrode and is formed to have a curved shape conforming to the shape of the head. The third mount part 212c is provided with a hole 212g for fixing an F3 measurement electrode.

The fourth mount part 212d is a plate-like member extending from the parietal region of the user to a C3 measurement electrode and is formed to have a curved shape conforming to the shape of the head. The fourth mount part 212d is provided with a hole 212h for fixing a C3 measurement electrode.

Further, the electrode mount 212 is provided with a hole 212i for fixing the electrode mount 212 to the headband 211. The electrode mount 212 may be fixed to the headband 211 through the hole 212i by screwing or the like. It should be noted that the headband 211 and the electrode mount 212 may be individually changed in size depending on the size of the head of the user.

By the six-electrode headgear 21 as described above, the measurement electrodes can be placed in the positions F3, F4, C3, C4, O1, and O2 that are defined by the International 10-20 system. This electrode placement is used for diagnosing a sleep disorder, for example.

The electroencephalographic apparatus 1 according to this embodiment has the configuration as described above.

[Operation of Electroencephalographic Apparatus]

As described above, in the electroencephalographic apparatus 1 according to this embodiment, due to the shape of its headband 111, the electrodes 114a to 114h are unlikely to be detached in biological signal measurement, in particular, in biological signal measurement during sleep. Even if the electrodes 114a to 114h are detached, the electrical contact is configured to be easily restored.

Figure 12:
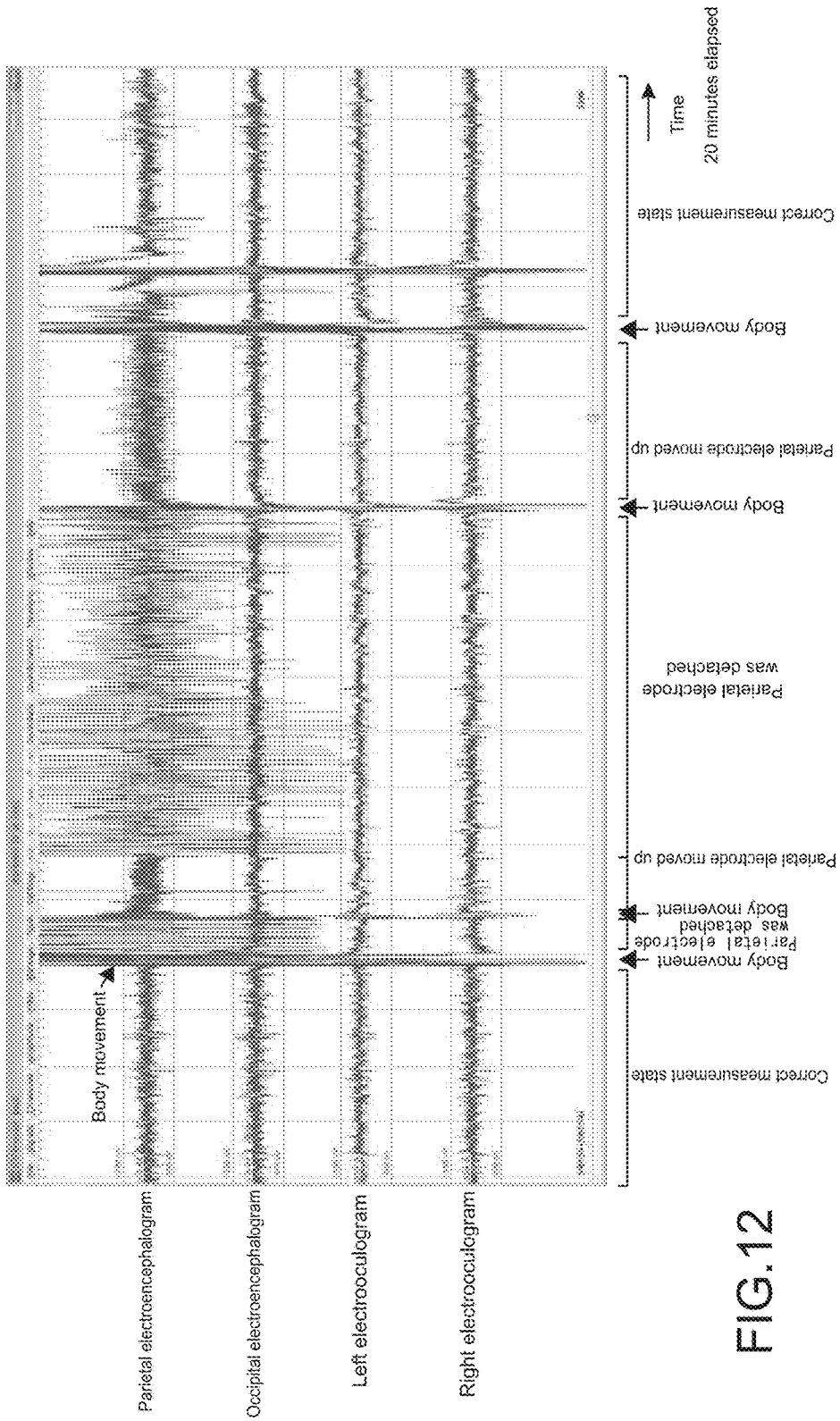
FIG. 12 is a view plotting a biological signal (electroencephalogram and electrooculogram) measured by each electrode of the electroencephalographic apparatus with respect to time.

FIG. 12 is a view plotting a biological signal (electroencephalogram and electrooculogram) measured by each electrode of the electroencephalographic apparatus 1 with respect to time. A "parietal electroencephalogram" is measured by the Cz measurement electrode 114c, an "occipital electroencephalogram" is measured by the Pz measurement electrode 114d, a "left electrooculogram" is measured by the left EEG electrode 114b, and a "right electrooculogram" is measured by the right EEG electrode 114a.

As shown in the figure, the area in which noise generates in the parietal electroencephalogram means a detached state of the Cz measurement electrode 114c from the scalp of the user. As can be seen, the noise starts to be reduced due to body movement, that is, the Cz measurement electrode 114c is restored.

Figure 13:
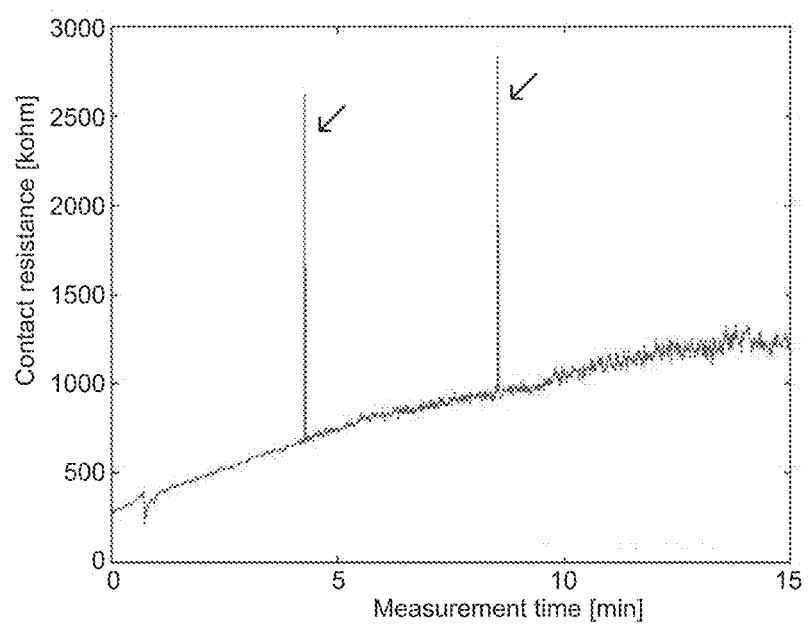
FIG. 13 is a graph plotting skin contact resistance measured by the electroencephalographic apparatus with respect to time.

Further, such electrode restoration can be also confirmed using skin contact resistance. The skin contact resistance is contact resistance between the electrode and the scalp and significantly increases when the electrode is detached from the scalp. FIG. 13 is a graph plotting skin contact resistance measured by the electroencephalographic apparatus 1 with respect to time. As shown in the figure, even when the skin contact resistance temporarily increases (shown by the arrows in the figure), the skin contact resistance temporarily returns to the original value. It can be said that even when the electrode is detached from the scalp, it can be restored.

As described above, in the electroencephalographic apparatus 1 according to this embodiment, when the headband 111 is attached to the head of the user, the first headband part 111a is placed to extend from the forehead to the upper portion of the occipital region, the second headband part 111b and the third headband part 111c branch off in opposite directions from the upper portion of the occipital region and arrive at the left and right mastoid regions. That is, the headband 111 is placed not to cover a portion from the connection point of each headband part in the upper portion of the occipital region to the lower portion of the occipital region. With this, when the user wearing the headgear 11 sleeps while lying on his back, the headband 111 does not abut against a pillow. Thus, it becomes possible to prevent misalignment of the headband 111 due to contact with the pillow, that is, detachment of each of the electrodes 114a to 114h.

In addition, the headband 111 is supported to hold the head of the user at the three points of the first abutting part 116, the second abutting part 117, and the third abutting part 118 with an elastic force. Therefore, even if the headband 111 strains due to roll-over of the user or the like so that each of the electrodes 114a to 114h is detached, it becomes possible that the elastic force of the headband 111 restores its shape so that the electrical contact of each of the electrodes 114a to 114h is restored.

Further, in the electroencephalographic apparatus 1 according to this embodiment, it is possible to attach/detach the main body 12 to/from the headgear 11, and hence it becomes possible to upgrade each of the main body 12 and the headgear 11, adjust the size of the headgear 11, change the application of the main body 12, and so on.

In addition, with the configuration of the main-body connection part 115, the main body 12 is fixed to the headgear 11 with flexibility, and hence it is possible to connect the main body not to interfere with the elastic deformation of the headband 111. With this, it becomes possible to ensure an elasticity necessary for restoration of each of the electrodes 114a to 114h when the headband 111 is misaligned, fitting to the head of the user, and the like.

In addition, by placing the right reference electrode 114g on the second abutting part 117 and placing the left reference electrode 114h on the third abutting part 118, the placement of the reference electrodes becomes possible only by wearing the headgear 11 without needs for additionally placing the reference electrodes.

As described above, according to the present disclosure, it is possible to provide the headband 111 capable of correctly placing the electrodes 114a to 114h on the head of the user, the headgear 11 including the headband 111, and the electroencephalographic apparatus 1 including the headgear 11.

The present disclosure is not limited to the above-mentioned embodiments and can be changed without departing from the gist of the present disclosure.

It should be noted that the present disclosure may also take the following configurations.

(1) A Headband Apparatus Comprising:
a plurality of headband portions integrally connected and configured to be positioned about a head of a user, wherein at least two headband portions are each configured to be positioned behind an ear.

(2) The headband apparatus of (1), wherein the at least two headband portions are configured so as to reduce movement during use.

(3) The headband apparatus of (1), wherein the at least two headband portions are spaced apart so as to be adapted to define an open area on a back region of the head, the open area including a parietal and an occipital region of the head.

(4) The headband apparatus of (1), wherein the at least two headband portions are configured to be positioned about a mastoid region of the head.

(5) The headband apparatus of (1), further comprising at least one headband portion configured to be positioned about a forehead region of the head.

(6) The headband apparatus of (5), wherein the at least one headband portion includes a first end configured to contact the forehead region and a second end configured to contact an upper portion of the occipital region.

(7) The headband apparatus of (6), wherein the at least two headband portions each include a third end connected to the second end of the first headband part and a fourth end that is configured to contact the mastoid region.

(8) The headband apparatus of (7), further comprising a plurality of abutting parts connected respectively to the fourth end of the at least two headband portions, the abutting parts including an elastic material configured to position the at least two headband portions to the mastoid region.

(9) The headband apparatus of (6), further comprising an abutting part connected to the first end of the at least one headband portion, the abutting part including an elastic material configured to position the at least one headband portion to the forehead region.

(10) The headband apparatus of (1), wherein the at least two headband portions are orthogonally formed with respect to the at least one headband portion.

(11) The headband apparatus of (1), wherein the at least two headband portions are orthogonally formed with respect to a third headband portion in a 'T-shape'.

(12) The headband apparatus of (1), wherein the plurality of headband portions include three headband portions, wherein the three headband portions include a plastic plate pattern based on a head dimension of the user, and wherein the three headband portions are shaped by bending and heating the three headband portions around a head pattern corresponding to the user.

(13) The headband apparatus of (1), wherein the plurality of headband portions consists of two headband portions.

(14) The headband apparatus of (1), wherein the plurality of headband portions consist of three headband portions including two headband portions and a third headband portion that is shaped to be positioned about a frontal region of the head.

(15) A headgear apparatus comprising:
a plurality of headband portions integrally connected and configured to be positioned about a head of a user, wherein at least two headband portions are each configured to be positioned behind an ear; and
a plurality of electrodes included within some of the headband portions that are configured to measure an electrical activity of the head.

(16) The headgear apparatus of (15), wherein at least one headband portion is configured to be positioned about a forehead region of the head and includes at least one of the electrodes.

(17) The headgear apparatus of (16), wherein the electrodes included within the at least one headband portion include a Cz measurement electrode and a Pz measurement electrode.

(18) The headgear apparatus of (15), wherein the at least two headband portions each include at least one of the electrodes that are configured to contact the mastoid region.

(19) The headgear apparatus of (15), wherein the electrodes included within the at least two headband portions include a P3 measurement electrode, a P4 measurement electrode, and reference electrodes.

(20) The headgear apparatus of (15), wherein the at least two headband portions are configured so as to reduce movement during use.

(21) An electroencephalograph apparatus comprising:
a plurality of headband portions integrally connected and configured to be positioned about a head of a user, wherein at least two headband portions are each configured to be positioned behind an ear;
a plurality of electrodes included within some of the headband portions are configured to measure an electrical activity of the head; and
a main body connection part included within at least one of the headband portions and electrically connected to the plurality of electrodes, the main body connection part configured to accommodate a detachable main body.

(22) The electroencephalograph apparatus of (21), further comprising a main body detachably connected to the main body connection part, the main body being configured to determine electroencephalogram data based on electrical signals received from the electrodes.

(23) The electroencephalograph apparatus of (22), wherein the main body includes:

a first circuit configured to covert the electrical signals measured by the electrodes into digital information; and a second circuit configured to process the digital information into the electroencephalogram data.

(24) The electroencephalograph apparatus of (22), wherein the main body includes a plurality of sensors configured to measure arterial oxygen saturation or naso-oral breathing.

(25) The electroencephalograph apparatus of (21), wherein:
at least one of the headband portions is configured to be positioned about a forehead region of the head and includes one of the electrodes, and
the at least two headband portions each including one of the electrodes that are each configured to contact the mastoid region.

(26) The electroencephalograph apparatus of (25), wherein:
the electrodes included within the at least one headband portion include a Cz measurement electrode and a Pz measurement electrode, and
the electrodes included within the at least two of the headband portions include a P3 measurement electrode, a P4 measurement electrode, and reference electrodes.

(27) The electroencephalograph apparatus of (21), wherein the electrodes are configured to be positioned on the head corresponding to an International 10-20 system.

(28) The electroencephalograph apparatus of (21), wherein the at least two headband portions are shaped so as to reduce movement while the user is sleeping.

(29) The electroencephalograph apparatus of (21), further comprising: a plurality of arm portions integrally connected to at least one of the headband portions, wherein at least two arm portions are configured to be positioned about temple a region of the head; and
an electrode included within each of the arm portions, each of the electrodes being configured to contact the temple region.

(30) The electroencephalograph apparatus of (29), wherein the electrodes included within the arm portions include EEG electrodes.

(31) The electroencephalograph apparatus of claim 21, wherein the main body connection part includes:
a screw hole;
a skirt that is provided around the screw hole; and a guide that is provided around the skirt.

(32) The electroencephalograph apparatus of (31), wherein the skirt is a tubular member including an elastomer and the guide is a tubular member including a synthetic resin.

(33) A headgear, including:
a headband including
a first headband part that extends from a forehead of a user to an upper portion of an occipital region of the user,
a second headband part that is connected to the first headband part and extends from the upper portion of the occipital region of the user, orthogonally to the first headband part, to a right mastoid region of the user, and
a third headband part that is connected to the first headband part and extends from the upper portion of the occipital region of the user, orthogonally to the first headband part, to a left mastoid region of the user; and
an electrode that is provided to the headband to be brought into contact with a scalp of the user.

(34) The headgear according to (33), in which
the first headband part includes a first abutting part that abuts against the forehead of the user,
the second headband part includes a second abutting part that abuts against the right mastoid region of the user,
the third headband part includes a third abutting part that abuts against the left mastoid region of the user, and
the headband is formed of an elastic material and is supported on the head of the user by the first abutting part pressing the forehead of the user, the second abutting part pressing the right mastoid region of the user, and the third abutting part pressing the left mastoid region of the user.

(35) The headgear according to (33) or (34), further including
a main-body connection part configured to detachably support a main body that houses an electronic circuit that processes an output signal of the electrode.

(36) The headgear according to any one of (33) to (35), in which
the main-body connection part includes
a screw hole,
a tubular skirt that is provided around the screw hole and is formed of a flexible material, and
a tubular guide that is provided around the skirt and is formed of a non-flexible material.

(37) The headgear according to any one of (33) to (36), in which
the electrode includes
a right reference electrode that is placed on the second abutting part to detect a reference potential, and
a left reference electrode that is placed on the third abutting part to detect a reference potential.

(38) An electroencephalographic apparatus, including:
a headgear including
a headband including
a first headband part that extends from a forehead of a user to an upper portion of an occipital region of the user,
a second headband part that is connected to the first headband part and extends from the upper portion of the occipital region of the user, orthogonally to the first headband part, to a right mastoid region of the user, and
a third headband part that is connected to the first headband part and extends from the upper portion of the occipital region of the user, orthogonally to the first headband part, to a left mastoid region of the user, and
an electrode that is provided to the headband to be brought into contact with a scalp of the user; and
a main body that is detachably connected to the headgear and houses an electronic circuit that processes an output signal of the electrode.

(39) A headband, including:
a first headband part that extends from a forehead of a user to an upper portion of an occipital region of the user;
a second headband part that is connected to the first headband part and extends from the upper portion of the occipital region of the user, orthogonally to the first headband part, to a right mastoid region of the user; and
a third headband part that is connected to the first headband part and extends from the upper portion of the occipital region of the user, orthogonally to the first headband part, to a left mastoid region of the user.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 1 electroencephalographic apparatus
11 headgear
12 main body
111 headband
111a first headband part
111b second headband part
111c third headband part
114a to 114h electrode
115 main-body connection part
116 first abutting part
117 second abutting part
118 third abutting part

What is claimed is:

1. A wearable headband apparatus, comprising:
   a plurality of headband portions; and
   a main body connection portion that includes:
      a screw hole,
      a skirt that surrounds the screw hole, and
      a guide that surrounds the skirt,
         wherein the main body connection portion is configured to connect a detachable main body to a first headband portion of the plurality of headband portions through the screw hole.

2. The wearable headband apparatus of claim 1, wherein a second headband portion of the plurality of headband portions and a third headband portion of the plurality of headband portions reduce a movement of the wearable headband apparatus.

3. The wearable headband apparatus of claim 1, wherein a second headband portion of the plurality of headband portions and a third headband portion of the plurality of headband portions are spaced apart.

4. The wearable headband apparatus of claim 1, wherein a second headband portion of the plurality of headband portions and a third headband portion of the plurality of headband portions are wearable on a mastoid region of a head of a user.

5. The wearable headband apparatus of claim 1, wherein the first headband portion of the plurality of headband portions is wearable on a forehead region of a head of a user.

6. The wearable headband apparatus of claim 5,
   wherein the first headband portion includes a first end and a second end, and
   wherein the first end is wearable on the forehead region of the head and the second end is wearable on an upper portion of an occipital region of the head.

7. The wearable headband apparatus of claim 6,
   wherein a second headband portion of the plurality of headband portions includes a third end and a fourth end,
   wherein a third headband portion of the plurality of headband portions includes a fifth end and a sixth end,
   wherein the third end and the fifth end are connected to the second end, and
   wherein the fourth end is wearable on a left mastoid region of the head and the sixth end is wearable on a right mastoid region of the head.

8. The wearable headband apparatus of claim 1, wherein each of a second headband portion of the plurality of headband portions and a third headband portion of the plurality of headband portions is orthogonal to the first headband portion of the plurality of headband portions.

9. The wearable headband apparatus of claim 1, wherein a second headband portion of the plurality of headband portions and a third headband portion of the plurality of headband portions are in a T-shape with the first headband portion of the plurality of headband portions.

10. The wearable headband apparatus of claim 1, wherein the first headband portion of the plurality of headband portions and a second headband portion of the plurality of headband portions are wearable behind an ear of a user.

11. The wearable headband apparatus of claim 1, wherein the skirt comprises a flexible material and the guide comprises a non-flexible material.

* * * * *